(12) United States Patent
Ruijten

(10) Patent No.: US 6,759,065 B1
(45) Date of Patent: Jul. 6, 2004

(54) EXTRACTION METHOD, PHARMACEUTICAL COMPOSITION AND A COSMETIC COMPOSITION

(75) Inventor: Henri M. Ruijten, Bussum (NL)

(73) Assignee: XenoBiosis, Amsterdam (NL)

( * ) Notice: Subject to any disclaimer, the term of this patent is extended or adjusted under 35 U.S.C. 154(b) by 0 days.

(21) Appl. No.: 09/719,901

(22) PCT Filed: Jun. 18, 1999

(86) PCT No.: PCT/NL99/00379

§ 371 (c)(1),
(2), (4) Date: Feb. 15, 2001

(87) PCT Pub. No.: WO99/65504

PCT Pub. Date: Dec. 23, 1999

(30) Foreign Application Priority Data

Jun. 18, 1998 (NL) .................................... 1009437

(51) Int. Cl.$^7$ ...................... A61K 35/78; A61K 31/44; A01N 43/08; C07D 498/00; C07D 407/00
(52) U.S. Cl. ................. 424/752; 424/725; 424/774; 514/783; 514/286; 514/468; 546/63; 549/297
(58) Field of Search ................. 424/95.1, 725, 424/752, 773, 774, 775, 776, 779; 426/534, 3, 583, 590, 650; 514/783, 286, 468; 546/63; 549/297

(56) References Cited

U.S. PATENT DOCUMENTS 4,831,133 A * 5/1989 Goodbody et al. ......... 540/478
5,352,777 A * 10/1994 Jhingan ..................... 536/25.4
5,399,348 A * 3/1995 Schwabe ................. 424/195.1

FOREIGN PATENT DOCUMENTS

CN 1167153 * 6/1997

OTHER PUBLICATIONS

Kaufman et al. Molecular and Cellular Methods in Biology and Medicine; 1995, CRC Press, Inc., Boca Raton, Florida, pp. 436–437.*

Brunori et al. The Use of Cellulase in the Isolation of In Vitro Plant Cell Nucelei Suitable for DNA Cytophotometry; Z Pflanzenphysiol. Bd.81.S. 95–101, 1977.*

Kaufman et al. Molecular and Cellular Methods in Biology and Medicine; 1995, CRC Press, Inc., Boca Raton, Florida, pp. 18–19.*

* cited by examiner

Primary Examiner—Patricia A Patten
(74) Attorney, Agent, or Firm—Kinney & Lange, P.A.

(57) ABSTRACT

A compound is extracted from vegetable material, wherein the vegetable material is reduced and treated with a solvent. According to the invention, the vegetable material is frozen using a liquid nitrogen and in frozen condition reduced in size. According to two important embodiments, the vegetable material comes from the ginkgo tree, in particular fresh leaves, and water is used as a solvent. The invention also relates to a pharmaceutical preparation and a cosmetic preparation comprising as active component a compound obtained by the method according to the invention.

13 Claims, No Drawings

EXTRACTION METHOD, PHARMACEUTICAL COMPOSITION AND A COSMETIC COMPOSITION

CROSS-REFERENCE TO RELATED APPLICATIONS

This application is a 371 of PCT/NL99/00379, filed Jun. 18, 1999, which claims priority from Dutch patent application serial number 1009437, filed Jun. 18, 1998.

FIELD OF THE INVENTION

The present invention relates to a method of extracting a compound from vegetable material, wherein the vegetable material is reduced in size, subjected to an extraction treatment using a solvent, after which the undissolved parts are separated from the solvent comprising the compound.

BACKGROUND OF THE INVENTION

This type of method is quite old. Examples are the infusion of tea and the preparation of tinctures. In both cases the undissolved parts are usually separated from the solvent comprising the compound. This may be accomplished by, for example, filtering or centrifugation.

The disadvantage with the known methods is that to a lesser or greater degree the active compound(s) stay behind in the separated insoluble parts.

The object of the present invention is to provide a method as described in the preamble, by which the yield of active compound can be increased.

To this end the method is characterized in that the vegetable material is frozen using a liquified gas and in frozen condition reduced in size prior to being extracted with the solvent.

In this invention the vegetable material is effectively opened up and a higher percentage of yield is assured. Liquid nitrogen is very suitable for this purpose because of its inert (non-oxidative) nature and low price.

European patent 0 477 968 describes a method of preparing an extract of Ginkgo biloba by treating the leaves with aqueous acetone, an aqueous alkanol with 1 to 3 C atoms, or anhydrous methanol at a temperature of 40–100° C. After the removal of solid parts, this solution is treated with ammonium sulphate, methyl ethyl ketone, and the resulting extract is extracted with a higher alkanol. After several additional steps an extract is obtained comprising 20 to % by weight of flavoglycosides, 2.5 to 4.4% by weight of ginkgolides A, B, C and J, and 2.0 to 4.0% by weight of bilobalide. The described method of extraction is very laborious.

European patent 0 431 535 describes a method of preparing an extract from Ginkgo biloba leaves that essentially corresponds with the method described above. In addition, lead salt is used for further purification. For this reason this extraction method is also very laborious while moreover using a lead compound that is bad for both the environment and human health.

DETAILED DESCRIPTION

According to an important embodiment, the vegetable material is chosen from a group comprising plant parts of the ginkgo tree (Ginkgo biloba) and Huperzia serrata.

Such vegetable material proves to extract excellently by the method outlined in the present invention at hand, yielding pharmaceutically high-grade solutions. Ginkgolides and flavonoids can be extracted from plant parts of the ginkgo tree. Huperzine can be isolated from plant parts of the Huperzia serrata. All these compounds possess interesting pharmaceutical properties.

The most preferable plant parts of the ginkgo tree to be used are fresh leaves which have been dried shortly before treatment, with water being used as the solvent.

Surprisingly, this method has proven that with fewer processing steps a purer product can be obtained. In the present application the term water is understood to mean a liquid comprised of mostly water that may contain up to 10% water-soluble alcohol or ketone, such as acetone. The water can also comprise salt, which prevents undesirable compounds from dissolving and/or assists the precipitation of such compounds. The water may also comprise enzymes that weaken the cell structure of the plant material. Though the pH can vary within a wide range, it will generally be lower than 7. In order to increase the level of flavonoids, the extracted leaves may be washed again with water to which a completely water-miscible organic solvent has been added, such as 40% acetone. The preparation of an extract from ginkgo leaves is known in the art. With this preparation the ginkgo leaves are dried after which they are extracted using alcohol or ketone, which may contain some water. In order to obtain a product with a sufficiently high content of active compound, further laborious refinement steps are necessary, increasing the cost of the product.

In order to obtain a high-grade product, the plant parts of the ginkgo tree should be obtained from a 1 to 15-year-old ginkgo tree, preferably from a 3 to 10-year-old tree and most preferably from a 5-year-old tree.

To obtain a preparation with a suitable ginkgolide/flavonoid ratio (such as 1:4 or higher), the pH of the water preferably lies between 4 and 7.

To further increase the yield, it is advantageous to add an enzyme such as cellulase to break down the cell walls after reduction.

Preferably extraction with water is then preformed for a maximum of 3 hours.

In order to ensure a high level of purity, the extraction treatment is suitably carried out at a temperature from 10 to 60° C., preferably 20 to 40° C.

One favourable embodiment for obtaining a composition containing the compound and having a long shelf life involves drying the solution containing the compound, which may conveniently be achieved by spray-drying or freeze-drying.

Suitably the solvent is eliminated from the solvent containing the compound, and the residue is extracted with a further solvent.

In this manner it is possible to obtain a purer preparation comprising the compound. For the extraction of ginkgo methylisobutylketone (MIK) or tert.-butylether (TBE) may conveniently be used.

In accordance with the above the invention also related to two preparations.

The invention relates in particular to a pharmaceutical preparation comprising an active component containing a compound obtained according to a method outlined by the invention, together with a pharmaceutically acceptable excipient or carrier.

Such a pharmaceutical preparations may be used, for example, to treat patients with Alzheimer's disease, patients with symptoms caused by prolonged contact with organic solvents, etc. The pharmaceutical preparations according to the invention can be administered in any form, particularly oral or parenteral administration will be preferred.

The invention also relates to a cosmetic preparation containing an active component comprised of a compound obtained according to a method outlined by the invention, together with a cosmetically acceptable topical carrier.

Such a cosmetic preparation can help to keep skin young and supple.

The invention will now elucidated with the aid of the following exemplary embodiment.

EXAMPLE 1

Within 72 hours of being picked, 10 g of ginkgo leaves are contacted with liquid nitrogen (3 ml). The ginkgo leaves are crushed using a porcelain mortar. Then 100 ml of water is added as well as 1:100% w/v of ULTRA-ZYME AFP-L and CELLUBRIX L. (Novo Nordisk Ferment Ltd., Switzerland); this is incubated for 2 hours at 50° C. and a pH or 5.5 while being mixed and subsequently extracted at a pH of 4–5. The liquid, containing as active components ginkgolides and flavonoids, is separated from the solid parts by means of filtering over a large-mesh filter and then subjected to microfiltration over, for example, a 0.2 μm hydrophilic filter and subsequently freeze-dried (extract A).

EXAMPLE II

The method described in Example I is repeated. In the same manner described above, the residue resulting from the extraction is extracted for 1 hour with 40% acetone solution and subsequently freeze-dried (extract B).

Water is added to both freeze-dried extracts A and B (0.1 g extract per ml water). The obtained solutions are extracted with (1:1 v/v) methylisobutylketone (MIK) or tert.-butylether (TBE). These extractions are repeated twice and the fractions are combined for each solvent. The solvents are evaporated by means of a film evaporator.

As it is difficult to adequately eliminate MIK, the residue is after evaporation dissolved in a 3:2 mixture of acetone and water (first acetone is added until the residue is dissolved, then gradually water is added under heating to 50° C. and sonication). Subsequently the acetone is evaporated and the aqueous solution is freeze-dried.

The resulting residues are analyzed with the aid of HPLC. A 150 * 3 mm ODS-3 Inertsil 5 column (Chrompack) was used. Isocratic elution, with as mobile phase methanol/water (for ginkgolides) or methanol/buffer 55/45 v/v (for flavonoids) was performed with 1 ml/min. Buffer composition: 1:2 g/l ammonium dihydrogen phosphate with phosphoric acid at pH=2.5.

Retention times for Bilobalide, Ginkgolide A and B: 4.9, 9.0 and 10.1 min. Detection by means of a refractive index detector.

Retention times for the flavonoids Quercetin, Kaempferol and Isorametine: 8.9, 15.5 and 16.9 min. Detection at 360 nm.

The date a summarized in Table I.

TABLE I

|     | Treatment | Ginkgolides *) | Flavonoids *) |
| --- | --- | --- | --- |
| I | water | (1, 57) | (0, 44) |
| II | water/acetone | (1, 20) | (1, 04) |
| III | I + MIK | 115 (35, 8) | 50, 8 (15, 8) |
| IV | II + MIK | 19, 9 (30, 8) | 24, 5 (38) |
|     | total | 134, 9 | 75, 3 |
| V | I + TBE | 79, 4 (51, 1) | 15, 4 (9, 9) |
| VI | II + TBE | 14, 0 (41, 3) | 5, 6 (16, 5) |
|     | total | 93, 4 | 21 |

*) in mg. The percentage of dry matter is indicated in brackets.

The above table shows that extraction with MIK and TBE improves the purity of the product. Extraction with MIK results in a higher yield, while extraction with TBE is useful if a higher yield of ginkgolides in relation to flavonoids is desired.

What is claimed is:

1. A method of extracting a composition comprising a compound from plant parts of Ginkgo Huperzia seratta comprising:

freezing the plant parts using a liquified gas;

reducing the size of the frozen plant parts;

adding an enzyme to break down cell walls of the plant parts of reduced size;

adding an extraction solvent to the enzyme treated plant parts to form a mixture; and removing undissolved parts from the mixture to produce an extraction composition comprising a compound, wherein the compound is selected from the group consisting of a ginkgolide a flavonoid, and huprazine.

2. A method according to claim 1, characterized in that the plant parts of the Ginkgo tree are fresh leaves, and water is the solvent.

3. A method according to claim 1, characterized in that the solvent is water, and the pH of the water is between 4 and 7.

4. A method according to claim 1, wherein the solvent acts on the enzyme treated plant parts for at least 1 to a maximum of 3 hours prior to the removing of; the undissolved parts.

5. A method according to claim 1, wherein the step of adding a solvent comprises:

maintaining the mixture at a temperature from 10 to 60° C.

6. A method according to claim 1, characterized in that after removing the undissolved parts from the mixture, the solvent is eliminated from the compound with a second solvent.

7. A method according to claim 1, characterized in that the plant parts of the Ginkgo tree are obtained from a 1 to 15-year-old Ginkgo tree.

8. A method according to claim 1, wherein the removing of undissolved parts is performed by filtering the mixture.

9. A method according to claim 8, further comprising:

microfiltration performed after the filtering step.

10. A method according to claim 8, further comprising:

drying the filtered mixture by spray-drying or freeze-drying.

11. A method according to claim 1, wherein the adding or an enzyme is performed prior to the adding an extraction solvent.

12. A method of preparing a composition comprising a compound comprising:

performing the method of claim 1 to obtain the composition and;

mixing the composition together with a pharmaceutically acceptable excipient or carrier for manufacture of a pharmaceutical preparation.

13. A method of preparing a composition comprising a compound comprising:

performing the method of claim 1 to obtain the composition and mixing the composition together with a cosmetically acceptable topical carrier for manufacture of a cosmetic preparation.

* * * * *

UNITED STATES PATENT AND TRADEMARK OFFICE
CERTIFICATE OF CORRECTION

PATENT NO. : 6,759,065 B1
DATED : July 6, 2004
INVENTOR(S) : Henri M. Ruijten

It is certified that error appears in the above-identified patent and that said Letters Patent is hereby corrected as shown below:

Column 1,
Line 32, delete "size", insert -- size, --
Line 34, delete "invention", insert -- manner --

Column 3,
Line 7, delete "1:100% w/v of ULTRA-ZYME", insert
-- 1:1000% w/v of ULTRA-ZYM --

Column 4,
Line 16, delete "ginkgolide a", insert -- ginkgolide, --
Line 24, delete "of;", insert -- of --

Signed and Sealed this

Twenty-second Day of March, 2005

JON W. DUDAS
*Director of the United States Patent and Trademark Office*